US008841570B2

(12) United States Patent
Vasilescu

(10) Patent No.: US 8,841,570 B2
(45) Date of Patent: Sep. 23, 2014

(54) SYSTEM AND METHOD FOR AFLATOXIN DETECTION

(75) Inventor: Mike Vasilescu, Clovis, CA (US)

(73) Assignee: Paramount Farms International LLC, Los Angeles, CA (US)

( * ) Notice: Subject to any disclaimer, the term of this patent is extended or adjusted under 35 U.S.C. 154(b) by 856 days.

(21) Appl. No.: 12/904,149

(22) Filed: Oct. 13, 2010

(65) Prior Publication Data

US 2012/0093985 A1  Apr. 19, 2012

(51) Int. Cl.
   *B07C 5/00* (2006.01)
   *G06T 7/00* (2006.01)
   *G06T 7/40* (2006.01)
   *G01N 33/02* (2006.01)

(52) U.S. Cl.
   CPC ..... *G06T 7/0004* (2013.01); *G06T 2207/10024* (2013.01); *G01N 33/02* (2013.01); *G06T 2207/30128* (2013.01); *G06T 7/408* (2013.01)
   USPC ........... 209/580; 209/44.2; 209/577; 209/587

(58) Field of Classification Search
   USPC ......... 209/44.2, 576, 577, 580, 587, 932, 939
   See application file for complete search history.

(56) References Cited

U.S. PATENT DOCUMENTS

| | | | |
|---|---|---|---|
| 3,305,089 A | 2/1967 | Fraenkel | |
| 4,181,853 A | 1/1980 | Abu-Shumays et al. | |
| 4,203,522 A | 5/1980 | Fraenkel et al. | |
| 4,285,698 A * | 8/1981 | Otto et al. | 436/20 |
| 4,535,248 A | 8/1985 | Schade et al. | |
| 4,630,736 A * | 12/1986 | Maughan et al. | 209/587 |
| 4,699,273 A * | 10/1987 | Suggi-Liverani et al. | 209/580 |
| 4,866,283 A | 9/1989 | Hill, Jr. | |
| 5,172,005 A * | 12/1992 | Cochran et al. | 250/559.08 |
| 5,520,290 A * | 5/1996 | Kumar et al. | 209/580 |
| 5,822,068 A * | 10/1998 | Beaudry et al. | 356/417 |
| 6,410,872 B2 * | 6/2002 | Campbell et al. | 209/577 |
| 6,786,221 B2 | 9/2004 | Lane | |
| 7,456,952 B2 * | 11/2008 | Walker | 356/317 |
| 8,384,046 B2 * | 2/2013 | Haidekker et al. | 250/459.1 |
| 8,563,934 B2 * | 10/2013 | Yao et al. | 250/339.12 |
| 2003/0025086 A1 * | 2/2003 | Stroka | 250/461.1 |
| 2008/0257793 A1 * | 10/2008 | Valerio | 209/567 |
| 2011/0117025 A1 * | 5/2011 | Dacosta et al. | 424/9.6 |
| 2012/0021101 A1 * | 1/2012 | Berghmans et al. | 426/231 |
| 2012/0228199 A1 * | 9/2012 | Modiano et al. | 209/587 |

OTHER PUBLICATIONS

De Mello, "Development of Physical and Optical Methods for In-shell . . ." Journal of Agricultural Science, vol. 1, No. 2 Dec. 2009, 12 pgs.

Hirano et al., "Near Infra Red Detection of Internally Moldy Nuts" Biosci. Biotechnol. Biochem, 62(1), 102-107, 1998.

Pearson et al. "Reduction of Aflatoxin and Fumonisin Contamination . . . " Cereal Chem. 81(4):490-498.

* cited by examiner

*Primary Examiner* — Joseph C Rodriguez
(74) *Attorney, Agent, or Firm* — Cotman IP Law Group, PLC

(57) ABSTRACT

A nondestructive system and method for aflatoxin detection based on red-orange fluorescence is described. A sorting plane is illuminated with a wide band black light source. At least one image of unsorted produce on said sorting plane is obtained. A red component of the at least one image is evaluated. Contaminated produce is determined based on the red component.

17 Claims, 9 Drawing Sheets

SYSTEM AND METHOD FOR AFLATOXIN DETECTION

BACKGROUND OF THE INVENTION

1. Field of the Invention

Embodiments of the invention described herein pertain to the field of agriculture. More particularly, but not by way of limitation, one or more embodiments of the invention enable a system and method for aflatoxin detection.

2. Description of the Related Art

In recent years researchers have identified many chemical compounds as carcinogenic. These include man-made compounds such as asbestos, and pesticides. On the other hand, naturally formed carcinogenic compounds also exist, including mycotoxins.

One prominent member of the mycotoxins family is aflatoxin. Aflatoxin is a product of the mold *Aspergillus jlavus*. Aflatoxins are highly aggressive toxins that negatively affect mammal's health and causing organ damage, especially in the liver. Aflatoxins include aflatoxin B1, aflatoxin B2, aflatoxin G1, and aflatoxin G2. *Aspergi/lusjlavus* mold requires a humid environment, and can proliferate in any medium such as fruits, cereals and nuts. The distribution of aflatoxins in agricultural products has a high level of randomness because mold growth is dependent on many variables, including humidity, wind, shade and other factors. The random distribution of aflatoxin in harvested crops is further increased due to multiple handling operations and processes, including partially or fully automated operations and processes.

Almonds, a tree nut, are susceptible to aflatoxin contamination. When the fruit is ripe, almonds are harvested by shaking almond trees with automated machines. Prior to harvest, orchard soil between rows of trees is cleared and vacuumed to eliminate rocks and other debris. Once the almonds have fallen on the cleared ground, they are swept to the center of the aisle and left there for the hull to dry for a period of up to 3 months. When the hull is dried, the almonds are gathered into trucks using large mechanized vacuum machines and transported to the hulling and shelling process plant. At the hulling and shelling process plant, the hull is removed and the shell is cracked and separated from the almond kernel. The almond kernels are then stored in bins, or silos. The storage atmosphere parameters, such as temperature and humidity, are controlled to minimize molding. While in storage, the almonds continue to dry to a final moisture content. The final moisture content is different from crop year to crop year and agricultural area. On average, the moisture content reaches a stable level of between about 3% to about 4.5%.

Human intoxication with aflatoxin is a serious concern in agricultural operations, including nut harvesting of nuts such as brazil nuts, peanuts, pistachios, walnuts, hazelnuts, pecans, cashews, macadamias, almonds and other nuts and produce. Aflatoxin contamination also generates other effects which reduce yield. To quantify costs associated with aflatoxin contamination with regard to process costs, we need to analyze the almond process flow. Highly random distribution of contamination, in conjunction with high health hazard to humans and animals, drove the U.S. Food and Drug Administration (FDA) and the European Food Safety Authority (EFSA) to establish stringent limits on total aflatoxin content. The maximum allowed total aflatoxin content is of 20 ppb (parts per billion) in the US and 110 ppb in the EU.

Previous research attempting to determine the correlation between aflatoxin and other variables in special storage humidity and harvest atmospheric conditions have failed to generate a predictive method or correlation between variables. Thus, addressing aflatoxin contamination necessarily focuses on the detection of aflatoxin in individual almond batches to eliminate contaminated nuts from the process stream.

There are two primary existing methods for aflatoxin detection: liquid chromatography (LC) and UV fluorescence. Liquid chromatography is a destructive laboratory testing method useful for extracting and separating aflatoxins to determine an aflatoxin concentration of the input product. Since laboratory methods of detection require the sample to be ground up and chemically treated, in a sense destroying the product, test validation is limited. Therefore, the usefulness of the method to remove contaminated nuts from a lot is limited. The results of the liquid chromatography method are at best an estimate of contamination levels for the rest of a batch from which the destroyed sample is obtained.

The UV fluorescence method consists of an excitation light in the UV band or blacklight (BL) spectrum. Once exposed to UV or BL radiation, aflatoxins become fluorescent and phosphorescent. The emitted radiation is evaluated to determine the presence of aflatoxins. Previous research shows a maximum excitation for aflatoxin can be achieved when incident light wavelength is between 360 nm and 390 nm. Based on exposure to BL, previous researches have mapped aflatoxin fluorescence below 580 nm. The Cole-Parmer Technical Library states that aflatoxins all have absorption maxima around 360 nm with a molar absorptivity of about 20,000, where the aflatoxin B toxins are named for their blue fluorescence (425 nm) and the G toxins for their green-blue fluorescence (450 nm). (Available at http://www.coleparmer.com/techinfo/techinfo asp?openlist=D,E,C&htmlfile=aflotoxin.htm). Radiation used in the UV fluorescence method for aflatoxin detection is characterized by wavelength and bandwidth. A light source generating a narrow band of incident light has been preferred to eliminate potential interference between detected fluorescence and incident light from the radiation source. One common element to typical systems and methods is the utilization of narrow band excitation UV light (360 to 365 nm bandwidth).

Existing detection equipment, including color sorting equipment, is constructed based on these results. However, this equipment fails to detect and eliminate aflatoxin contaminated almonds to reduce aflatoxin contamination to an acceptable level. Color sorters employ two light sources and two cameras, which individually take a snap shot of each nut face, one nut at a time. U.S. Pat. No. 4,866,283, entitled "Optical Inspection of Food Products," is directed to aflatoxin detection in peanuts using laser excitation. The method points out that BL cannot be used for aflatoxin detection because incident and emitted lights reside within the same spectral bandwidth domain. However this research points to an excitation wave length of 363 and an aflatoxin Fluorescence with a maximum pick at 575 nm.

U.S. Pat. No. 4,285,698, entitled "Analysis of Aflatoxins in Peanuts by High Pressure Liquid Chromatograph," is directed to a method for determining the presence and concentration of aflatoxins in peanuts. A process is described for the chemical extraction of aflatoxin from ground peanuts, which is separated into aflatoxin B1, B2, G1 and G2 using high-pressure liquid chromatography. A fluorescence detector with an excitation filter of 365 nm and an emission filter of 425 nm is used to quantify the aflatoxin present.

U.S. Pat. No. 4,535,248, entitled "Method for Detecting Aflatoxin in Almonds," is directed to a method for the detection of aflatoxin in almonds compatible with an almond sorting machine. The aflatoxin is detected as determined by violet-purple fluorescence in response to UV light with a wavelength from 320-400 nm.

There are several limitations to the state of the art of aflatoxin detection and testing. Aflatoxin fluorescence is limited to surface present contaminant. At the same time, destructive laboratory testing of individual nuts is not feasible. The random distribution of aflatoxin in a lot, which may range in size up to 20 metric tons (approximately 44,000 lbs), makes it difficult for a destructive test to ensure with a 99% accuracy the absence of contaminant. These limitations cause costly results in the commercial production of almonds. For example, a lot of 80,000 lbs. of almonds may pass aflatoxin quality standards for shipping to the EU for an approximate cost of 3,500.00 US Dollars. However, the lot may be sampled and rejected due to the random distribution of contamination. In this scenario, the lot must be shipped back to the USA for re-processing. The entire lot is than re-processed trough color sorters and hand sorting and re-sampled. The re-processed lot may be exported a second time. In this scenario, the shipping cost exceeds 10,000.00 US Dollars.

To overcome the problems and limitations described above there is a need for an improved system and method for aflatoxin detection.

BRIEF SUMMARY OF THE INVENTION

One or more embodiments of systems and methods for aflatoxin detection disclosed herein are based on red-orange fluorescence or phosphorescence of aflatoxin compounds excited with black light (BL).

As used herein, the term "black light (BL)" refers to electromagnetic radiation composed primarily of near-ultraviolet (UV) wavelengths with a low visible light component.

As used herein, the term "fluorescence" refers to the emission of light by any composition due to light absorbed at a different wave length.

As used herein, the term "phosphorescence" refers to the emission of light by any composition due to light absorbed at a different wave length, where the emission of light does not occur immediately after absorption.

As used herein, the term "destructive testing" refers to any testing process that requires substantial alteration of input product. In one or more instances, destructive testing renders the input product unsuitable for human consumption or sale in the input product form.

As used herein, the term "non-destructive" testing refers to any testing process that does not substantially alter the input product. In one or more cases, the output product of non-destructive testing is still fit for human consumption and sale.

As used herein, the term "liquid chromatography" (LC) refers to the separation of molecules dissolved in a liquid which are passed through a gel, stationary phase that separates the molecules in the original mixture.

One or more embodiments of systems and methods for aflatoxin detection are directed to a nondestructive method for aflatoxin detection based on red-orange fluorescence. The nondestructive method for aflatoxin detection includes illuminating a sorting plane with a wide band black light source, where the sorting plane is configured to move produce through a process flow system.

The nondestructive method for aflatoxin detection further includes obtaining at least one image of unsorted produce on the sorting plane. The produce may include nuts such as almonds, pistachios or other nuts and produce where there is a need to detect the presence of aflatoxin.

The nondestructive method for aflatoxin detection further includes evaluating a red component of the at least one image.

The nondestructive method for aflatoxin detection further includes determining contaminated produce based on the red component.

The nondestructive method for aflatoxin detection further includes removing the contaminated produce from the sorting plane.

In one or more embodiments, the at least one image includes a plurality of single nut images, where removing the contaminated produce includes removing nuts corresponding to single nut images in which contamination is detected based on the red component.

In one or more embodiments, evaluating the red component includes detecting the presence of light of about 620 nm to about 720 nm wavelength.

In one or more embodiments, the at least one image includes an RGB image, where the imaging device is configured to determine that contaminated produce is present by evaluating a red channel of the RGB image. However the use of other color spaces able to isolate the desired wavelength are also within the scope and spirit of the invention and may be utilized to implement one or more aspects of the invention.

One or more embodiments of systems and methods for aflatoxin detection are directed to a computer readable medium encoded with computer readable instructions. Execution of the computer readable instructions causes one or more processors to execute steps. The process steps include obtaining at least one RGB image of at least one nut on a sorting plane illuminated with a wide band black light source.

The process steps further include evaluating red channel values in at least a portion of the RGB image from 0 to 255, inclusive.

The process steps further include determining that contaminated produce is present based on the presence of red channel values above a threshold red channel value, where the threshold red channel value is at least about 150. In one or more embodiments, the threshold red channel value is at least about 180. In one or more embodiments, the threshold red channel is at least about 210.

The process steps further include transmitting instructions to a separation device to remove from the sorting plane at least one contaminated nut corresponding to contaminated produce detected in at least one of the at least one RGB image.

One or more embodiments of systems and methods for aflatoxin detection are directed to a nondestructive aflatoxin detection system based on red-orange fluorescence detection.

The nondestructive aflatoxin detection system includes a sorting plane configured to receive unsorted produce from a produce source. The produce may include nuts. In one or more embodiments, the produce includes but is not limited to almonds.

The nondestructive aflatoxin detection system further includes at least one wideband black light source configured to illuminate the unsorted produce.

The nondestructive aflatoxin detection system further includes at least one imaging device configured to capture at least one image of the unsorted produce. In one or more embodiments, the at least one imaging device is further configured to filter light below about 400 nm to about 410 nm wavelength.

The nondestructive aflatoxin detection system further includes a image processing device coupled with the at least one imaging device, where the image processing device is configured to evaluate a red component of the at least one image of the unsorted produce, where the image processing device is further configured to determine contaminated produce present in the unsorted produce based the red component.

The nondestructive aflatoxin detection system further includes at least one separation device coupled with the image processing device, where the separation device is configured to remove the contaminated produce from the sorting plane.

In one or more embodiments, the nondestructive aflatoxin detection system further includes at least one powered component configured to drive a process flow to move bulk unsorted produce from the produce source on the sorting plane, where the process flow includes a first imaging stage and a second separation stage.

In one or more embodiments, the nondestructive aflatoxin detection system further includes an enclosure configured to eliminate other light sources from a chamber comprising the sorting plane, the at least one wideband black light source, and at least an entrance pupil location of the at least one imaging device.

In one or more embodiments, the at least one image includes a plurality of single nut images, where the at least one separation device is configured to remove contaminated nuts corresponding to images in which contamination is detected by the image processing device.

In one or more embodiments, the image processing device is configured to determine that contaminated produce is present when light of about 620 nm to about 720 nm wavelength is detected.

In one or more embodiments, the at least one image includes an RGB image, and where the imaging device is configured to determine that contaminated produce is present by evaluating a red channel of the RGB image.

In one or more embodiments, evaluating the red channel includes generating a red band histogram of red channel values in at least a portion of the RGB image from 0 to 255, inclusive, and where the imaging device is configured to determine contaminated produce by the presence of red channel values above a threshold red channel value, where the threshold red channel value is at least about 150. In one or more embodiments, the threshold red channel value is at least about 180.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION

A SYSTEM AND METHOD FOR AFLATOXIN DETECTION will now be described. In the following exemplary description numerous specific details are set forth in order to provide a more thorough understanding of the various embodiments within which one may implement the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the concepts and ideas described herein. Readers should note that although examples of the invention are set forth herein, the claims themselves, and the full scope of any equivalents, are what define the invention.

Figure 1:
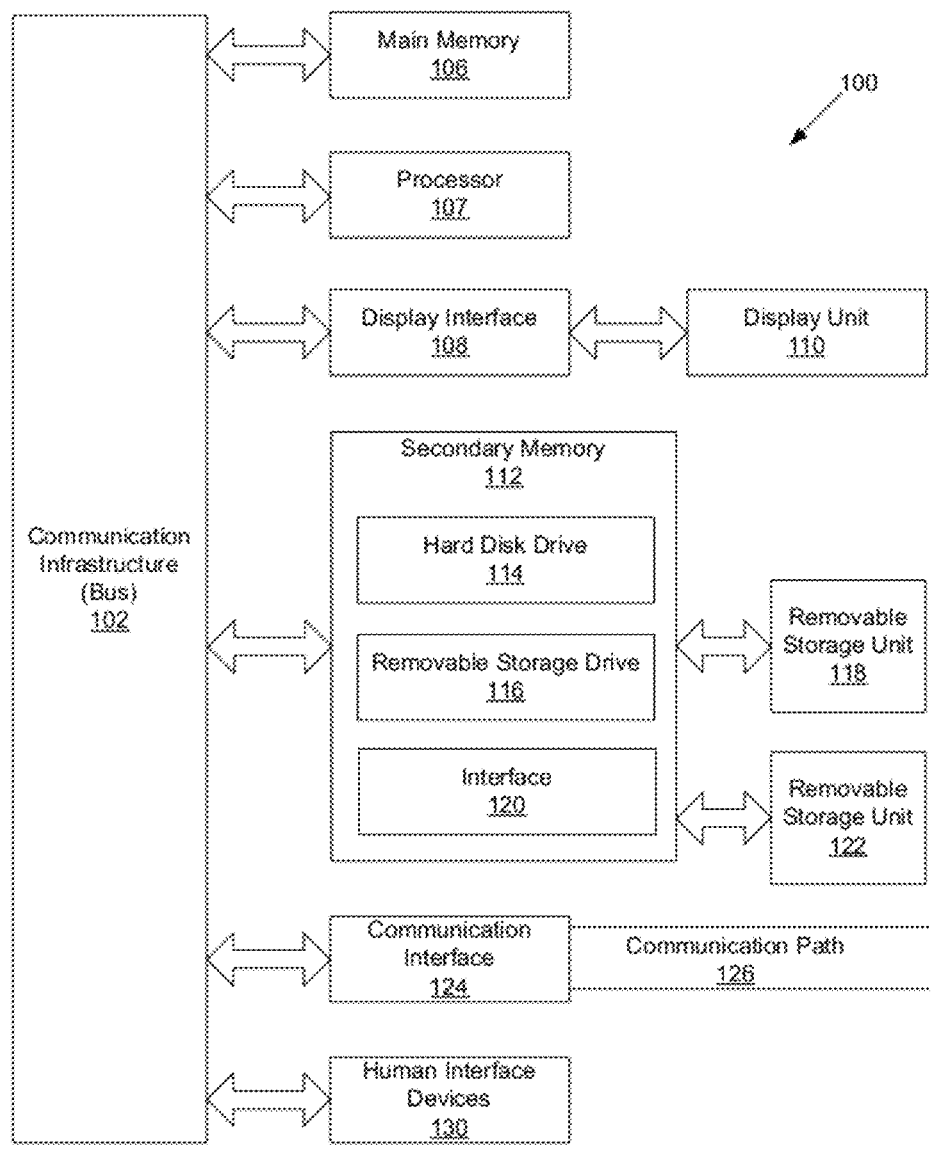
FIG. 1 illustrates a general-purpose computer and peripherals that when programmed as described herein may operate as a specially programmed computer capable of implementing one or more methods, apparatus and/or systems of the solution.

FIG. 1 diagrams a system 100 comprising a general-purpose computer and peripherals, when programmed as described herein, may operate as a specially programmed computer capable of implementing one or more methods, apparatus and/or systems of the solution described in this disclosure. The details of the general-purpose computer and peripherals are described herein for purposes of enablement and to highlight the notion that embodiments of the invention described herein may be implemented in a machine specially programmed to execute the functions and methods described herein. Readers familiar with the elements of a general-purpose computer may skip forward to paragraph [0062]. Processor 107 may be coupled to bi-directional communication infrastructure 102 such as communication infrastructure system bus 102. Communication infrastructure 102 may generally be a system bus that provides an interface to the other components in the general-purpose computer system such as processor 107, main memory 106, display interface 108, secondary memory 112 and/or communication interface 124. In one or more embodiments of systems and methods for digital hair coloring, one or more Graphical Processing Units (GPUs) are utilized to accelerate one or more graphic rendering processes.

Main memory 106 may provide a computer readable medium for accessing and executing stored data and applications. Display interface 108 may communicate with display unit 110 that may be utilized to display outputs to the user of the specially-programmed computer system. Display unit 110 may comprise one or more monitors that may visually depict aspects of the computer program to the user. Main memory 106 and display interface 108 may be coupled to communication infrastructure 102, which may serve as the interface point to secondary memory 112 and communication interface 124. Secondary memory 112 may provide additional memory resources beyond main memory 106, and may generally function as a storage location for computer programs to be executed by processor 107. Either fixed or removable computer-readable media may serve as Secondary memory 112. Secondary memory 112 may comprise, for example, hard disk 114 and removable storage drive 116 that may have an associated removable storage unit 118. There may be multiple sources of secondary memory 112 and systems implementing the solutions described in this disclosure may be configured as needed to support the data storage requirements of the user and the methods described herein. Secondary memory 112 may also comprise interface 120 that serves as an interface point to additional storage such as removable storage unit 122. Numerous types of data storage devices may serve as repositories for data utilized by the specially programmed computer system. For example, magnetic, optical or magnetic-optical storage systems, or any other available mass storage technology that provides a repository for digital information may be used.

Communication interface 124 may be coupled to communication infrastructure 102 and may serve as a conduit for data destined for or received from communication path 126. A network interface card (NIC) is an example of the type of device that once coupled to communication infrastructure 102 may provide a mechanism for transporting data to communication path 126. Computer networks such Local Area Networks (LAN), Wide Area Networks (WAN), Wireless networks, optical networks, distributed networks, the Internet or any combination thereof are some examples of the type of communication paths that may be utilized by the specially program computer system. Communication path 126 may comprise any type of telecommunication network or interconnection fabric that can transport data to and from communication interface 124.

To facilitate user interaction with the specially programmed computer system, one or more human interface devices (HID) 130 may be provided. Some examples of HIDs that enable users to input commands or data to the specially programmed computer may comprise a keyboard, mouse, touch screen devices, microphones or other audio interface devices, motion sensors or the like, as well as any other device able to accept any kind of human input and in turn communicate that input to processor 107 to trigger one or more responses from the specially programmed computer are within the scope of the system disclosed herein.

While FIG. 1 depicts a physical device, the scope of the system may also encompass a virtual device, virtual machine or simulator embodied in one or more computer programs executing on a computer or computer system and acting or providing a computer system environment compatible with the methods and processes of this disclosure. Where a virtual machine, process, device or otherwise performs substantially similarly to that of a physical computer system, such a virtual platform will also fall within the scope of disclosure provided herein, notwithstanding the description herein of a physical system such as that in FIG. 1.

One or more embodiments are configured to enable the specially programmed computer to take the input data given and transform it into a web-based UI by applying one or more of the methods and/or processes described herein. Thus the methods described herein are able to transform a stored component into a web UI, using the solution disclosed here to result in an output of the system as a web UI design support tool, using the specially programmed computer as described herein.

Figure 2:
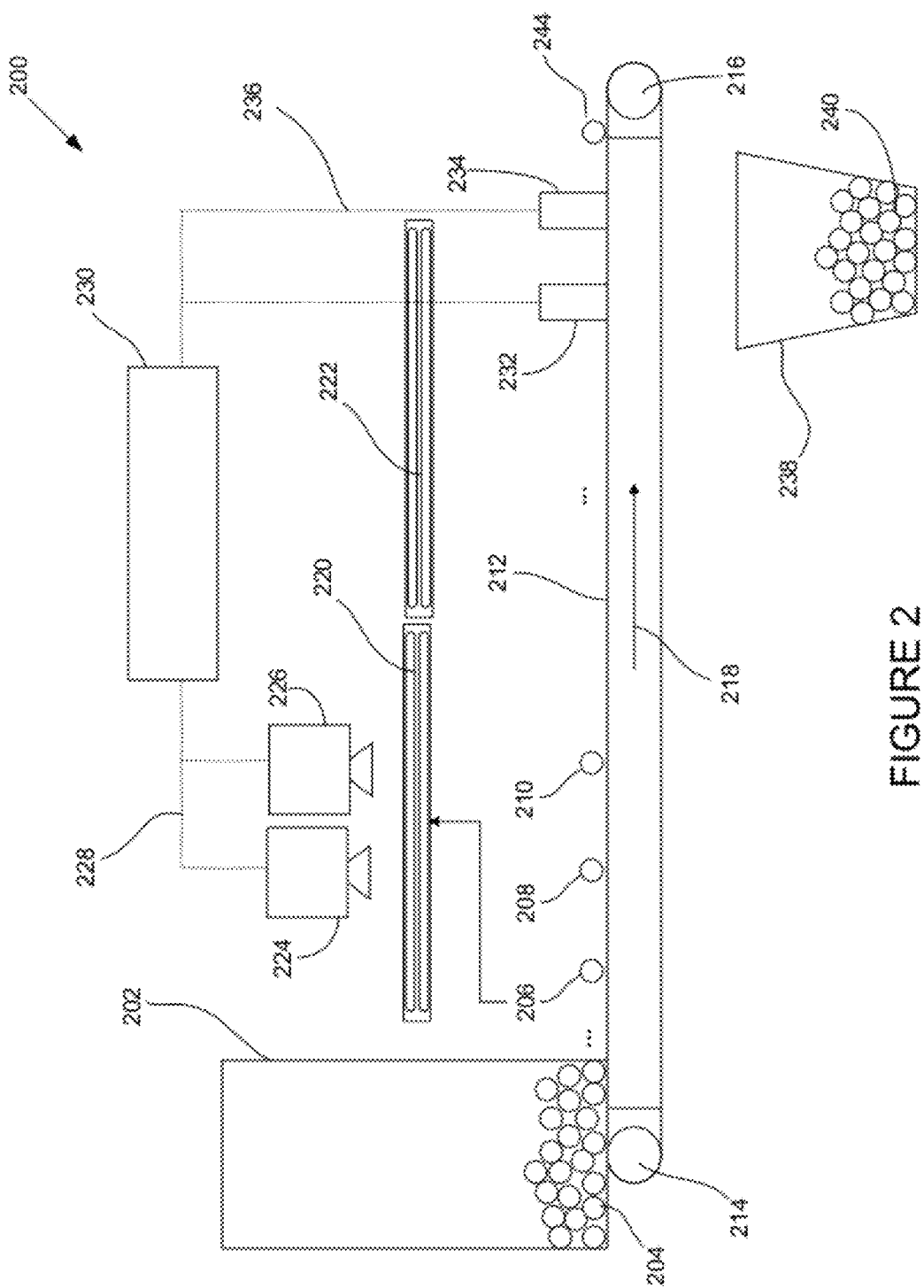
FIG. 2 illustrates an exemplary apparatus in accordance with one or more embodiments of systems and methods for aflatoxin detection.

FIG. 2 illustrates an exemplary apparatus in accordance with one or more embodiments of systems and methods for aflatoxin detection. Aflatoxin detection system 200 is a non-destructive aflatoxin detection system that may be partially or fully automated. Aflatoxin detection system 200 is typically an integrated process in a series of handling operations and processes.

Aflatoxin detection system 200 includes produce source 202. Produce source 202 may include any produce storage for bulk unsorted produce 204. In one or more embodiments, produce source 202 is the output of another handling operation and/or process. Bulk unsorted produce 204 may include any produce potentially contaminated with aflatoxin, including cereals, spices, and nuts, such as peanuts, almonds, pistachios, walnuts, brazil nuts, and any other tree or ground nut. In one or more embodiments, bulk unsorted produce 204 includes almonds.

Aflatoxin detection system 200 further includes sorting plane 212. In one or more instances, sorting plane 212 is configured to move unsorted produce 206-210 from produce source 202 through aflatoxin detection system 200. For example, sorting plane 212 may be configured to move unsorted produce 206-210 in a process flow direction 218. Sorting plane 212 is typically a conveyor belt but may be any other plane capable of moving unsorted produce 206-210 in a process flow direction 218. Sorting plane 212 may include one or more separate surfaces placed in proximity with each other. Sorting plane 212 may further include one or more trajectory in space through which produce travels, such as a gravity feed, a trajectory due to applied force, or any combination thereof.

In one or more embodiments, aflatoxin detection system 200 is configured to move unsorted produce 206-210 through a first imaging stage, placed on a horizontal, vertical and /or angled configuration plane and a second separation stage placed on a horizontal, vertical and /or angled configuration plane. Aflatoxin detection system 200 may include at least one process driving mechanism 214-216 configured to move unsorted produce 206-210. Process driving mechanism 214-216 may include motors, gears, pulleys, chains, inclines, chutes, and any other combination of powered and/or mechanical components and/or gravity. Process driving mechanism 214-216 may further include one or more electronic control components configured to control timing, speed, or any other factor.

Aflatoxin detection system 200 further includes at least one black light source 220-222. In one or more embodiments, black light source 220-222 includes one or more wide band black light sources. As used herein, the term "narrow band black light" refers to electromagnetic radiation where substantially all wavelengths are between about 360-365 nm. As used herein, the term "wide band black light" refers to any black light outside of the narrow band black light range, such as 355-370 nm. Wide band black light may be substantially wider than narrow band black light. For example, black light source 220-222 may have a maximum wave length pick centered at about 370 nm, with a bandwidth of approximately +/−50 nm. Black light source 220-222 may be positioned at any angle relative to sorting plane 212 and any other black light source 220-222. In one or more embodiments, multiple black light sources 220-222 are positioned to illuminate substantially all surfaces of unsorted produce 206-210 in sorting plane 212. In one or more embodiments, at least one mirror may be employed to illuminate unsorted produce 206-210 with light from black light source 220-222.

Aflatoxin detection system 200 further includes at least one imaging device 224-226. Imaging devices 224-226 are positioned to capture images of unsorted produce 206-210 on sorting plane 212, where unsorted produce 206-210 is illuminated by light from at least one black light source 220-222. In one or more embodiments, imaging devices 224-226 are configured to capture a plurality of single-nut images. Imaging devices 224-226 may be positioned at any angle relative to sorting plane 212 and black light sources 220-222. In one or more embodiments, multiple imaging devices 224-226 are positioned to capture substantially all surfaces of unsorted produce 206-210 in sorting plane 212. In one or more embodiments, at least one mirror may be employed to assist imaging devices 224-226 to capture all surfaces of unsorted produce 206-210. Imaging devices 224-226 may further include one or more filters configured to eliminate at least a portion of light wavelengths generated by black light source 220-222. For example, imaging devices 224-226 may be configured to filter wavelengths below about 400 nm, about 410 nm, or about 420 nm. The light may be filtered with one or more physical or digital filters. In one or more embodiments, imaging devices 224-226 include one or more sensors configured to automatically filter light below a filter wavelength. Imaging devices 224-226 may include at least one digital imaging device configured to capture light in the visible light range, such as an off-the-shelf consumer digital camera.

Aflatoxin detection system 200 further includes image processing device 230. Image processing device 230 may include one or more processors configured to evaluate a red component of the at least one image of unsorted produce 206-210. Image processing device 230 is further configured to determine contaminated produce present in unsorted produce 206-210 based the red component of the image captured by imaging device 224-226. Image processing device 230 may include one or more solid-state and/or software components. In one or more embodiments, aflatoxin detection system 200 includes one or more image processing devices 230. The operation of image processing device 230 is shown in more detail at FIGS. 2-3.

Image processing device 230 is coupled with imaging devices 224-226 via image communication channel 228. Image communication channel 228 may be any channel capable of transferring digital information between imaging devices 224-226 and image processing device 230, including a system bus, a network connection, a wired connection, a wireless connection, or any other channel of communication, including any combination thereof Image processing device 230 is coupled with separation devices 232-234 via separation communication channel 236. Separation communication channel 236 may be any channel capable of transferring digital information between separation devices 232-234 and image processing device 230, including a system bus, a network connection, a wired connection, a wireless connection, or any other channel of communication, including any combination thereof Aflatoxin detection system 200 further includes at least one separation device 232-234. Separation devices 232-234 are configured to remove unsorted produce 206-210 from sorting plane 212. Image processing device 230 is configured to transmit instructions to separation devices 232-234 via separation communication channel 236, where the instructions indicate contaminated produce for removal by separation devices 232-234. In one or more embodiments, image processing device 230 is configured to calculate a precise timing and/or location. Image processing device 230 may be configured to either transmit the timing and/or location information to separation devices 232-234, or alternately, to control separation devices 232-234 based on the timing and/or location information.

Separation devices 232-234 may utilize any method for removing an object from a surface and/or plane, including any method that applies the mechanical force or utilizes a gravitational force. In one or more embodiments, separation devices 230-234 apply force via air and/or vacuum to remove contaminated produce.

In one or more embodiments, produce removed by separation devices 232-234 is collected in one or more compartments 238 configured to hold bulk of contaminated produce 240. The output of aflatoxin detection system 200 is the sorted non-contaminated produce 244.

Figure 3:
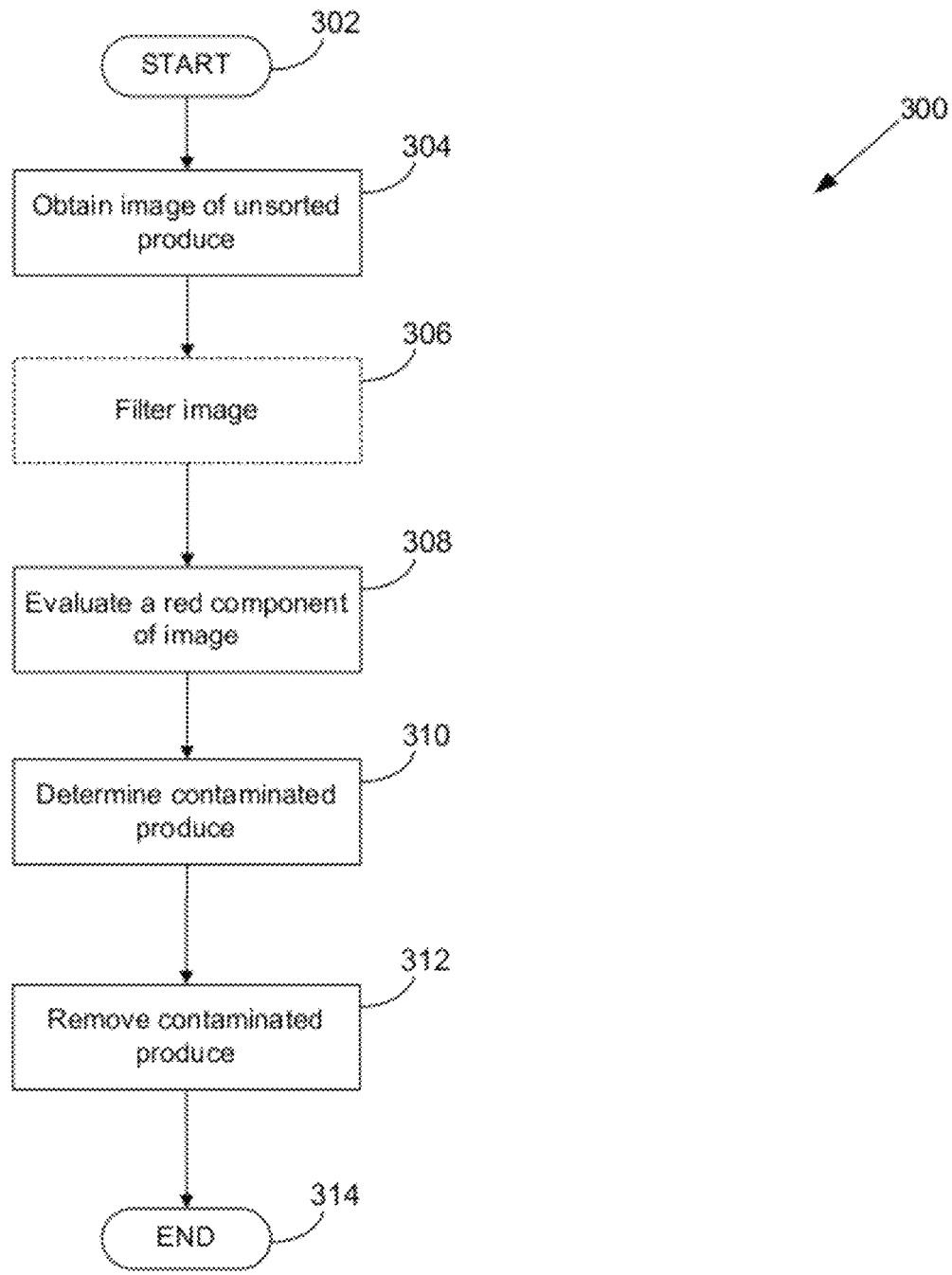
FIG. 3 illustrates an exemplary method in accordance with one or more embodiments of systems and methods for aflatoxin detection.

FIG. 3 illustrates an exemplary method in accordance with one or more embodiments of systems and methods for aflatoxin detection. Process 300 starts at step 302.

Processing continues to step 304, where an image of unsorted produce is obtained. The unsorted produce may include any produce potentially contaminated with aflatoxin, including cereals, spices, and nuts, such as peanuts, almonds, pistachios, walnuts, brazil nuts, and any other tree or ground nut. In one or more embodiments, the unsorted produce includes almonds. In one or more embodiments, the image is a single-nut image.

Processing continues to optional step 306, where the image is filtered. One or more imaging devices may be configured to filter light below a filter threshold, such as approximately 400 nm, 410 nm, or 420 nm. The light may be filtered with one or more physical or digital filters. In one or more embodiments, the imaging devices include one or more sensors configured to automatically filter light below a filter wavelength, such as an off-the-shelf consumer digital camera configured to capture visible light.

Processing continues to step 308, where the red component of the image is evaluated. In one or more embodiments, the evaluation includes detecting or approximating the presence of light of about 620 nm to about 720 nm wavelength in the image. In one or more embodiments, the images in RGB image, and the evaluation is based on processing the red channel of the RGB image.

Processing continues to step 310, where it is determined whether or not the unsorted produce associated with the image is contaminated with aflatoxin.

Processing continues at step 312, where the contaminated produce is removed.

Processing continues to step 314, where process 300 terminates.

Figure 4:
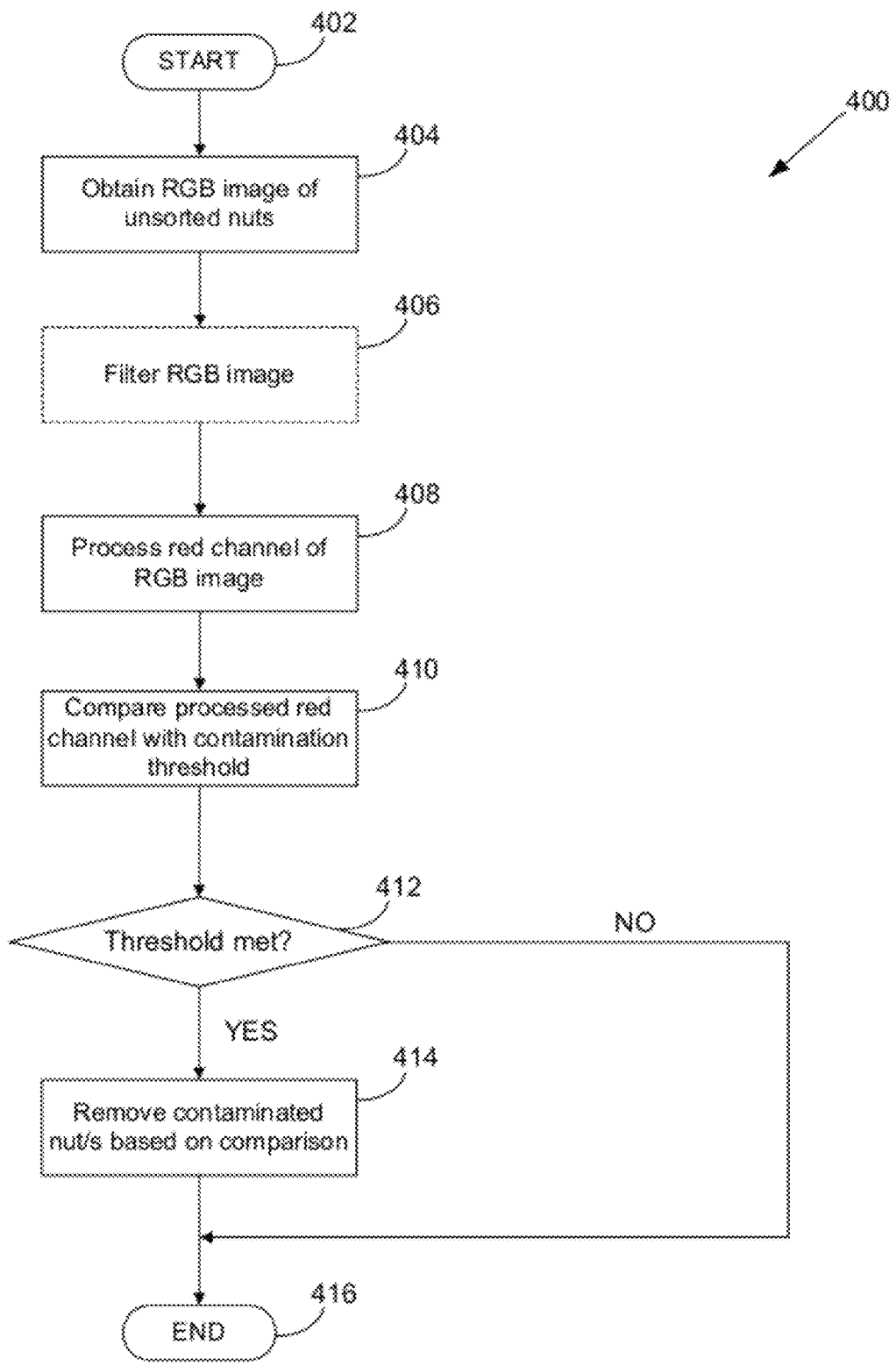
FIG. 4 illustrates an exemplary method in accordance with one or more embodiments of systems and methods for aflatoxin detection.

FIG. 4 illustrates an exemplary method in accordance with one or more embodiments of systems and methods for aflatoxin detection. Process 400 starts at step 402.

Processing continues to step 404, where an RGB image of unsorted nuts is obtained. The unsorted nuts may include any tree nut or ground nut, such as peanuts, almonds, pistachios, walnuts, brazil nuts, and any other tree or ground nut. In one or more embodiments, the unsorted nuts include almonds. In one or more embodiments, the RGB image is a single-nut image.

Processing continues to optional step 406, where the RGB image is filtered. One or more imaging devices may be configured to filter light below a filter threshold, such as approximately 400 nm, 410 nm, or 420 nm. The light may be filtered with one or more physical or digital filters. In one or more embodiments, the imaging devices include one or more sensors configured to automatically filter light below a filter wavelength, such as an off-the-shelf consumer digital camera configured to capture visible light.

Processing continues to step 408, where a red channel of the RGB image is processed. In one or more embodiments, processing the RGB image includes generating a red band histogram of red channel values in at least one portion of the RGB image from 0 to 255.

Processing continues to step 410, where the processed red channel is compared with a contamination threshold. In one or more embodiments, the processed red channel includes a red band histogram of red channel values in at least one portion of the RGB image from 0 to 255, and the contamination threshold is a threshold red channel value. In one or more embodiments, the threshold red channel value is at least about 150. In one or more embodiments, there are threshold red channel value is at least about 180. In one or more embodiments, there are threshold red channel value is at least about 210.

Processing continues to decision step 412, where it is determined whether or not the contamination threshold has been met. In one or more embodiments, the contamination threshold is met if all or substantially all red channel values in a red band histogram are below the threshold red channel value.

If the contamination threshold has been met, processing continues to step 414, where the contaminated nut is removed.

Processing continues to step 416, where process 400 terminates.

EXAMPLE 1

Experimental Setup

In a dark room, a separation table was set up. A wide band BL lamp was selected based on one or more factors, including cost. A BL lamp model 7020 E-BL manufactured by Lights of America, with a Light Bulb RB17T8BL was placed on top of the table at a distance of 30 cm. The BL lamp model is a 17 Watt wide band (360 nm to 520 nm bandwidth) "Fluorescent Tube".

Between about 5-10 pounds of machine-rejected almonds were collected. The machine-rejected almonds were rejected by a blue-green fluorescence color-sorter. Samples of almonds were separated by hand from the machine-rejected almonds. Each sample included about 50 grams of almonds.

Sample BL-Aflatoxin was selected by hand based on visual inspection for red fluorescence in the presence of BL.

Sample BL-Blanched was selected based on the presence of yellow, yellow-brown, blue and dark spots indicative of other damage after blanching a portion of the sampled almonds to remove the almond skin.

Four Machine-Rejected samples were selected based on the lack of red fluorescence. These machine-rejected samples, selected from the almonds rejected by a blue-green fluorescence color-sorter, are used as a control to show the inadequacy of the blue-green fluorescence color-sorter.

Upon completion of separation, images were collected for all test samples. Images of the samples were taken using an imaging device. The imaging device selected was a Fujifilm color "S1000fd" 10.0 Mega Pixels camera. The S1000fd, an off-the-shelf camera for digital photography, captures light in the visible spectrum, filtering light above about 400-410 nm. The S1000fd was also used to capture an image of the BL source for analysis and comparison. After this non-destructive imaging procedure, the six samples were tested using destructive LC testing.

A BL source image was also collected using the imaging device.

EXAMPLE 2

Liquid Chromatography Testing

Destructive Liquid Chromatography ("LC") analysis was performed on the six samples to identify an aflatoxin level for each sample. Individual samples were sent for aflatoxin testing at Paramount Farms Laboratory where the samples were tested by LC.

EXAMPLE 3

Image Analysis

Fluorescent pictures taken of the samples were further processed for color content analysis. A series of single-nut images were cropped from the sample images. The single-nut images were then further processed. Specifically, the red channel of the RGB color space images was used to generate corresponding red band histograms.

The single-nut images were selected to emulate an image of an individual nut generated and evaluated in color-sorting equipment. A BL-Aflatoxin single-nut image (image a) was selected from the BL-Aflatoxin sample image. A BL-Blanched Dark Spot single-nut image (image b-d) was selected from the BL-Blanched sample image. A BL-Blanched Yellow Spot single-nut image (image b-y) was selected from the BL-Blanched sample image. A Machine-Rejected single-nut image (image mr) was selected from the Machine-Rejected sample image. A portion of the BL source image (image s) was also selected to evaluate the incident light.

The single-nut images and source image (a, b-d, b-y, mr, s) were processed with the Image Tool function of Matlab. A histogram was produced for the Red color only, using the following Matlab syntax: >>figure, imhist(letter designation (:,:,1));

Each sample was evaluated to generate a sample histogram of the amplitude of light in the red band wavelength in the image based on a pixel count. The histogram on a scale from 0 to 255, with 0 associated with dark red and 255 associated with light red.

EXAMPLE 4

LC Results

Based on destructive LC testing, the BL-Aflatoxin sample proved to have B1, B2, G1, and G2 components with an Aflatoxin total sum of 251.884 ppm. The control BL-Blanched sample had a aflatoxin total sum of 0.123 ppm. All 4 machine reject samples had an aflatoxin total sum of <0.5 ppm. A sum that is less than 0.5 ppm is considered noise. These results are presented in Table 1:

TABLE 1

| aflatoxin levels in samples based on destructive LC testing | |
|---|---|
| Sample Type (number of samples) | Aflatoxin level (ppb) |
| BL-Aflatoxin (1) | 251.9 |
| BL-Blanched (1) | <0.5 |
| Machine Reject (4) | <0.5 |

From these results, we conclude that sample BL-Aflatoxin is an aflatoxin contaminated sample, while sample BL-blanched and the four Machine Reject samples are non-contaminated samples.

EXAMPLE 5

Image Analysis Results

Figure 5:
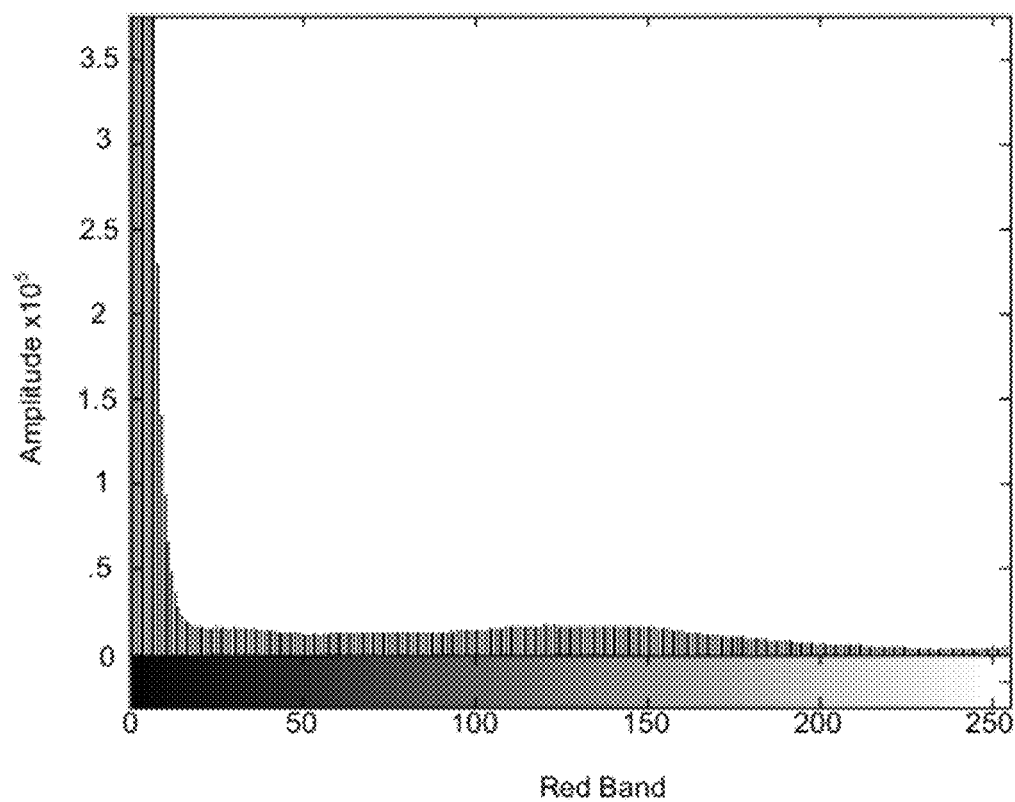
FIG. 5 illustrates an exemplary histogram produced by image analysis of an image of a sample contaminated with aflatoxin under BL in accordance with one or more embodiments of systems and methods for aflatoxin detection.
Figure 6:
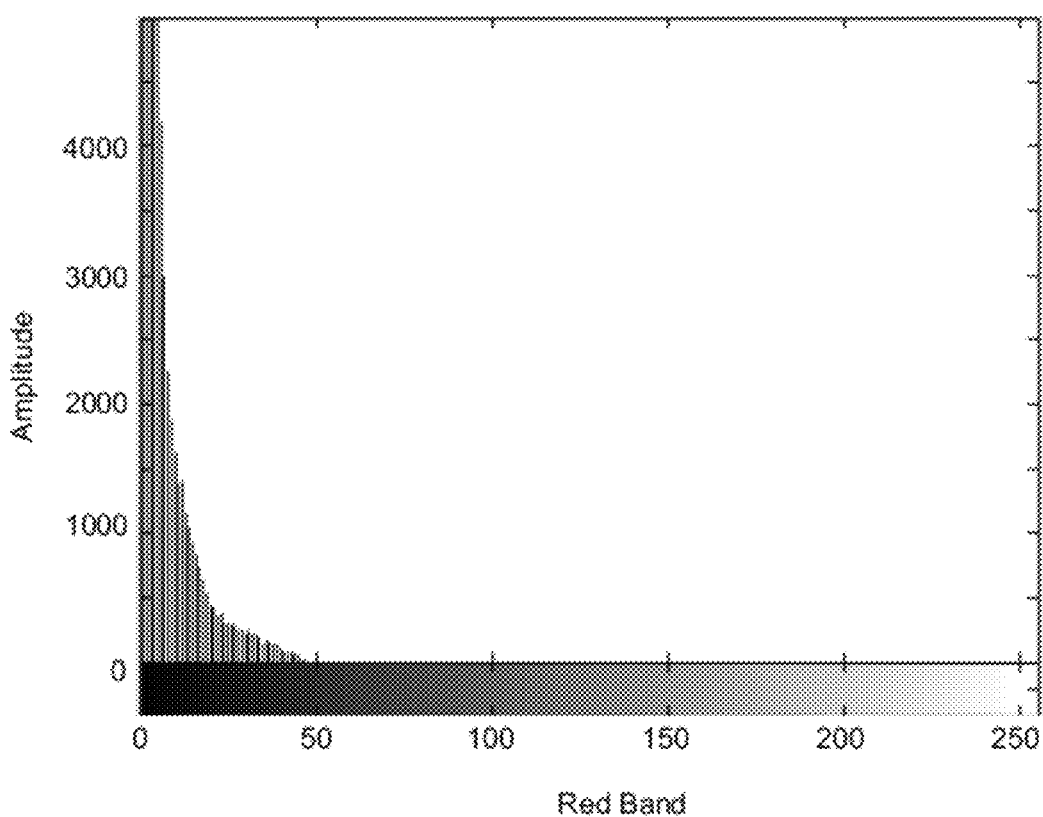
FIG. 6 illustrates an exemplary histogram produced by image analysis of an image of blanched damaged almonds with dark spotting under BL in accordance with one or more embodiments of systems and methods for aflatoxin detection.
Figure 7:
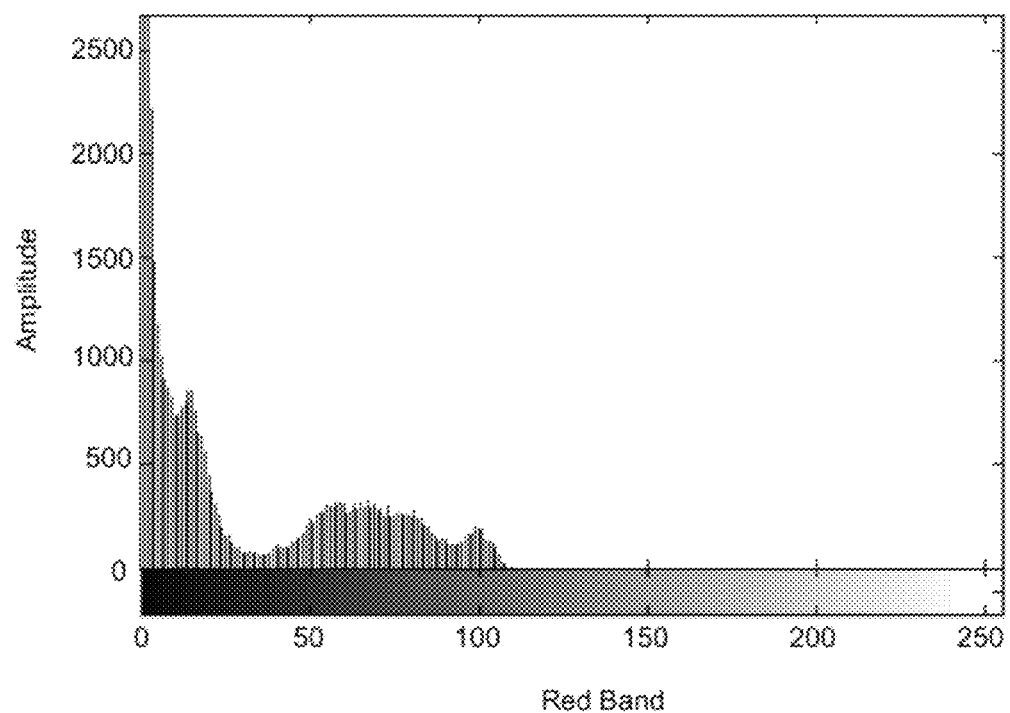
FIG. 7 illustrates an exemplary histogram produced by image analysis of an image of blanched damaged almonds with yellow spotting under BL in accordance with one or more embodiments of systems and methods for aflatoxin detection.
Figure 8:
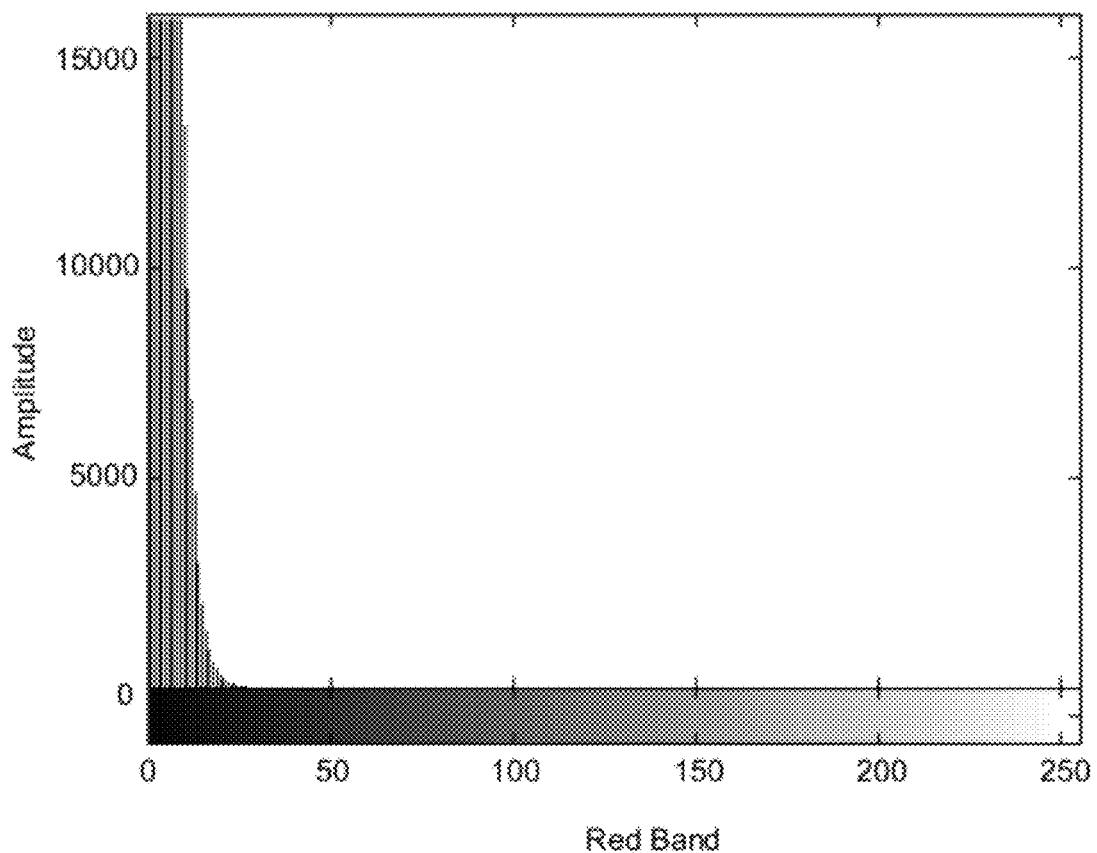
FIG. 8 illustrates an exemplary histogram produced by image analysis of an image of machine-rejected natural almonds in accordance with one or more embodiments of systems and methods for aflatoxin detection.
Figure 9:
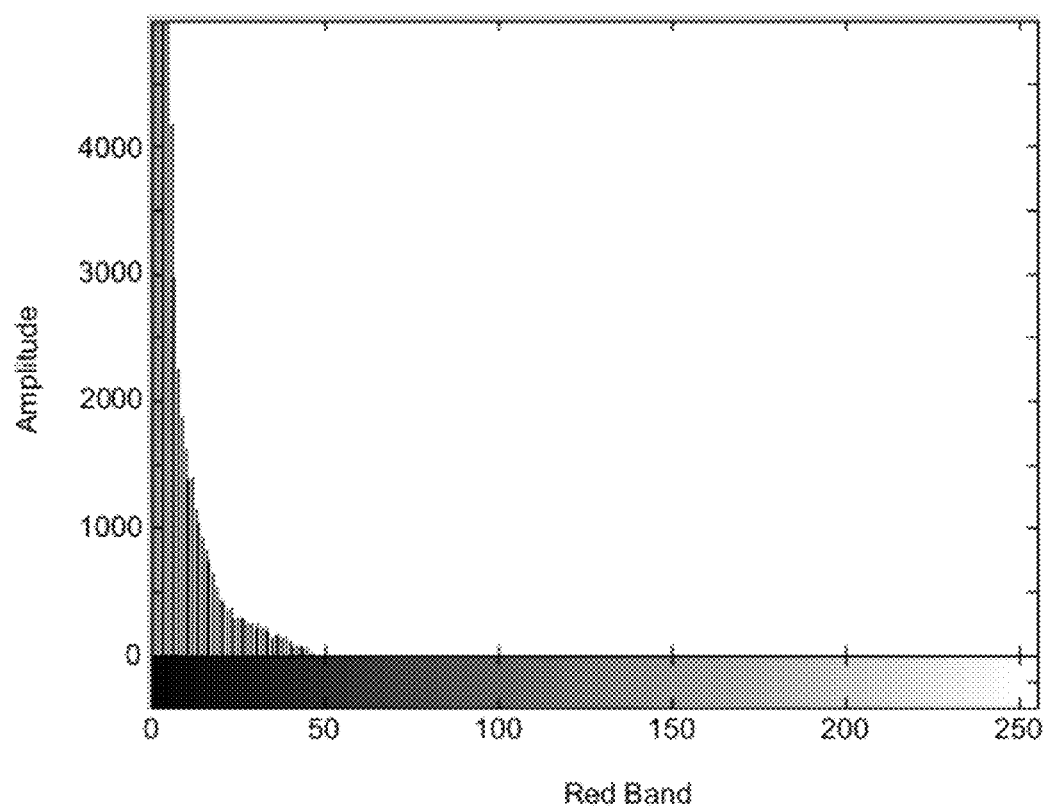
FIG. 9 illustrates an exemplary histogram produced by image analysis of an image of a broad spectrum UV light source in accordance with one or more embodiments of systems and methods for aflatoxin detection.

FIGS. 5-9 show red band histogram data produced by image analysis of the single-nut images. FIG. 5 illustrates histogram data produced based on image a, selected from the BL-Aflatoxin sample image. FIG. 6 illustrates histogram data produced based on image b-d, selected from the BL-Blanched sample image. FIG. 7 illustrates histogram data produced based on image b-y, selected from the BL-Blanched sample image. FIG. 8 illustrates histogram data produced based on image mr, selected from the Machine Reject sample image. FIG. 9 illustrates histogram data produced based on image s, selected from the BL source image.

As seen in FIG. 9, the red band histogram data for image s drops off at about $50^{th}$ shade of red, indicating that the wide band BL source does not produce detectable light of the color $(r',g,b)$, where $50<=r'<256$, $0<=g<=256$, $0<=b<=256$, in the RGB color space.

Based on LC testing, single-nut images b-d, b-y, and mr were selected from non-contaminated samples. As seen in FIGS. 6-8, the red band histogram data for images b-d, b-y, and mr dropped off at about 150th shade of red, indicating that light captured in an image of a non-contaminated nut surface does not produce detectable light of the color $(r'',g,b)$, where $150<=r''<256$, $0<=g<=256$, $0<=b<=256$, in the RGB color space.

Based on LC testing, single-nut image a was selected from an aflatoxin-contaminated sample. As seen in FIG. 5, the red band histogram data for image a includes all shades of red, indicating that light captured in an image of a non-contaminated nut surface does produces detectable light for all $r^a$ of the color $(r^a,g,b)$, where $0<=r^a<256$, $0<=g<=256$, $0<=b<=256$, in the RGB color space.

Table 2 shows the maximum shade of red in each histogram produced based on the single-nut images.

TABLE 2 value of red present in histogram data

| single-nut image | Aflatoxin ppb | Max Value |
|---|---|---|
| Aflatoxin (a) | 251.9 | 256 |
| Dark spot (b-d) | <0.5 | 50 |
| Yellow spot (b-y) | <0.5 | 110 |
| Machine-Rejected (mr) | <0.5 | 150 |
| BL source(s) | n/a | 120 |

While the invention herein disclosed has been described by means of specific embodiments and applications thereof, numerous modifications and variations could be made thereto by those skilled in the art without departing from the scope of the invention set forth in the claims.

What is claimed is:

1. A nondestructive aflatoxin detection system comprising:
   a chamber comprising an imaging stage and a sorting stage;
   a sorting plane in said chamber configured to receive bulk unsorted produce from a produce source, said sorting plane further configured to move said unsorted produce from said imaging stage through said sorting stage;
   at least one wideband black light source configured to illuminate said unsorted produce and highlight aflatoxin in said unsorted produce at said imaging stage;
   at least one imaging device at said imaging stage configured to capture at least one image consisting of Red, Green, and Blue component channels of said unsorted produce;
   an image processing device configured with at least one processor and computer memory coupled with said at least one imaging device, wherein said image processing device is configured to evaluate said Red component channel of said at least one image of said unsorted produce, wherein said image processing device is further configured to determine contaminated produce based on evaluation of said Red component channel in said at least one image of said unsorted produce; and
   at least one separation device in said sorting stage coupled with said image processing device, wherein said separation device is configured to remove said contaminated produce from said sorting plane.

2. The aflatoxin detection system of claim 1, further comprising a drive mechanism coupled to said sorting plane.

3. The aflatoxin detection system of claim 2, wherein said produce comprises nuts.

4. The aflatoxin detection system of claim 3, wherein said nuts comprises almonds.

5. The aflatoxin detection system of claim 3, wherein said at least one separation device is configured to remove contaminated nuts corresponding to images in which contamination is detected by said image processing device.

6. The aflatoxin detection system of claim 1, wherein said chamber is configured to eliminate other light sources except said at least one wideband black light source.

7. The aflatoxin detection system of claim 1, wherein said at least one imaging device is further configured to filter light below about 400 nm to about 410 nm wavelength.

8. The aflatoxin detection system of claim 1, wherein said image processing device is configured to determine that contaminated produce is present when light of about 620 nm to about 720 nm wavelength is detected.

9. The aflatoxin detection system of claim 1, wherein said evaluating said Red component channel comprises generating a red band histogram of Red component channel values in at least a portion of said at least one image from 0 to 255, inclusive, and wherein said image processing device is configured to determine contaminated produce by the presence of Red component channel values above a threshold Red component channel value, wherein said threshold Red component channel value is at least about 150.

10. The aflatoxin detection system of claim 9, wherein said threshold Red component channel value is at least about 180.

11. A nondestructive aflatoxin detection system comprising:
    a chamber comprising an imaging stage and a sorting stage, wherein said chamber is configured to isolate external light sources;
    a sorting plane in said chamber configured to receive bulk unsorted produce from a produce source, said sorting plane further configured to move said unsorted produce from said imaging stage through said sorting stage;
    at least one wideband black light source, at said imaging stage of said chamber, configured to illuminate said unsorted produce and highlight aflatoxin in said unsorted produce;
    at least one imaging device at said imaging stage configured to capture at least one image consisting of Red, Green, and Blue component channels of said unsorted produce;
    an image processing device configured with at least one processor and computer memory coupled with said at least one imaging device, wherein said image processing device is configured to evaluate said Red component channel of said at least one image of said unsorted produce, wherein said image processing device is further configured to determine contaminated produce based on evaluation of said Red component channel in said at least one image of said unsorted produce; and at least one separation device in said sorting stage coupled with said image processing device, wherein said separation device is configured to remove said contaminated produce from said sorting plane.

12. The aflatoxin detection system of claim 11, further comprising a drive mechanism coupled to said sorting plane.

13. The aflatoxin detection system of claim 12, wherein said at least one separation device is configured to remove contaminated nuts corresponding to images in which contamination is detected by said image processing device.

14. The aflatoxin detection system of claim 11, wherein said at least one imaging device is further configured to filter light below about 400 nm to about 410 nm wavelength.

15. The aflatoxin detection system of claim 11, wherein said image processing device is configured to determine that contaminated produce is present when light of about 620 nm to about 720 nm wavelength is detected.

16. The aflatoxin detection system of claim 11, wherein said evaluating said Red component channel comprises generating a red band histogram of Red component channel values in at least a portion of said at least one image from 0 to 255, inclusive, and wherein said image processing device is configured to determine contaminated produce by the presence of Red component channel values above a threshold red component value, wherein said threshold Red component channel value is at least about 150.

17. The aflatoxin detection system of claim 16, wherein said threshold Red component channel value is at least about 180.

* * * * *